United States Patent [19]

Sitek

[11] 4,398,836
[45] Aug. 16, 1983

[54] CALORIMETER

[75] Inventor: George J. Sitek, Stevensville, Mich.

[73] Assignee: Leco Corporation, St. Joseph, Mich.

[21] Appl. No.: 239,675

[22] Filed: Mar. 2, 1981

[51] Int. Cl.³ .................. G01K 17/00; G01N 25/16
[52] U.S. Cl. ................................................. 374/38
[58] Field of Search ............... 23/51; 73/15 B, 190 R, 73/190 CV, 191; 364/557, 577; 141/128, 242; 374/31, 36, 38

[56] References Cited

U.S. PATENT DOCUMENTS

| 550,943 | 12/1895 | Carpenter | 73/191 |
|---|---|---|---|
| 1,103,915 | 7/1914 | Junkers | 73/190 |
| 1,247,998 | 11/1917 | Parr | 73/191 |
| 3,285,053 | 11/1966 | Mazieres | 73/15 |
| 3,456,490 | 7/1969 | Stone | 73/15 |
| 3,593,577 | 7/1971 | Monner | 73/190 |
| 3,599,666 | 8/1971 | Curtis et al. | 141/128 |
| 3,650,306 | 3/1972 | Lancaster | 141/242 |
| 3,978,325 | 8/1976 | Goldstein et al. | 364/357 |

OTHER PUBLICATIONS

Shin et al., "Precision Isoperibol Calorimeter with Data Acquisition and Processing" in Review of Scientific Inst., vol. 46, #8, pp. 1043-1046, 8/75.
Aitken et al., "New Design of a Vacuum Jacket Precision Combustion Calorimeter" in Review of Scientific Inst., vol. 25, #10, 10/54, pp. 967-970.

Primary Examiner—Herbert Goldstein
Attorney, Agent, or Firm—Price, Heneveld, Huizenga & Cooper

[57] ABSTRACT

A calorimeter vessel includes a base for supporting a bomb thereon and a downwardly concavely opening container sealably engaging the base. The base includes a water supply system permitting a common water supply to supply water to three such vessels which include water level detecting sensors also permitting automatic filling of the vessels. In the preferred embodiment the vessel is filled in two stages providing rapid yet precise filling of each of the vessels. In one embodiment of the invention a microprocessor control circuit is employed for sampling temperature data within each of the vessels during an analysis to ascertain beginning and ending temperatures and for calculating the resultant heat of combustion of a sample. The microprocessor also is employed to automatically control the filling and emptying of the vessel and the firing of the sample containing calorimeter bomb.

25 Claims, 7 Drawing Figures 4,398,836

CALORIMETER

BACKGROUND OF THE INVENTION

The present invention relates to a calorimeter vessel and system for determining the heat of combustion of a sample.

Precision calorimeters typically include open top vessels in which a bomb for combusting a specimen is immersed in a manually filled vessel containing a pedetermined volume of water. The vessel is closed at the top and water circulated while monitoring its temperature initially and after the sample has been combusted to determine the change in temperature due to the energy content within the specimen. Either isothermal or adiabatic methods can be employed to determine the gross heat of combustion of hydrocarbon fuel samples calculated either in BTU's per pound, calories per gram, or other units. Prior art isothermal and adiabatic methods are disclosed in the American Society for Testing Materials Standard D2382-76 published in September of 1976 which described the construction of a calorimeter as well as methods of calculating the gross heat of combustion based upon temperature measurements employing such structure.

SUMMARY OF THE PRESENT INVENTION

The system of the present invention employs an isothermal-type method of determining the heat of combustion or energy content of hydrocarbon fuels such as coal, oil and the like. The present invention represents a significant improvement over manual prior art calorimeter vessels and provides control circuit means permitting early firing of the calorimeter bomb and which rapidly determines the resultant heat of combustion of a sample.

Apparatus embodying the present invention includes a calorimeter vessel having a base defining a support for the calorimeter bomb and a downwardly concavely opening container which sealably engages the base defining therein a sealed volume which is filled with water before an analysis. According to one aspect of the invention, the system includes means for rapidly and automatically filling the vessel with water once sealed. Temperature detecting means positioned within the calorimeter vessel is coupled to circuit means for sampling the water temperature at periodic intervals. The circuit means of the preferred embodiment includes a microprocessor for correlating initial temperature readings to calculate an initial temperature representative of the temperature at which the slope of the temperature readings would initially stabilize and for firing the calorimeter bomb at a predetermined time. The microprocessor also samples the temperature data to determine when the temperature slope becomes constant after firing and extrapolates the temperature representative data to ascertain the final temperature such that the temperature differential and the energy content of the sample can be determined. In one embodiment, a plurality of vessels are coupled to a common source of water and share a common control circuit.

Thus, the present invention includes an improved calorimeter vessel, and in one embodiment an improved control system for sampling temperature data to permit early firing of the calorimeter bomb. According to another feature of the invention, one or more calorimeter vessels are automatically filled to a precise volume of water.

These and other features, objects and advantages of the present invention will become apparent upon reading the following description thereof together with reference to the drawings in which:

DETAILED DESCRIPTION OF THE PREFERRED EMBODIMENT

Figure 1:
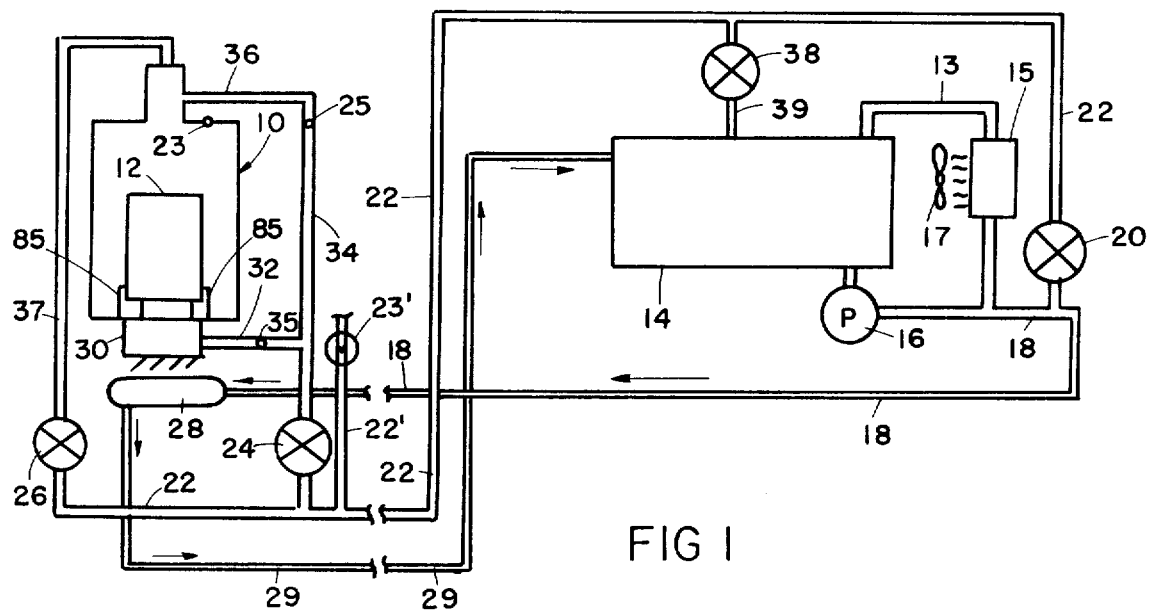
FIG. 1 is a diagram in schematic form of the system of the present invention.

Referring initially to FIG. 1 there is shown a calorimeter which includes a vessel 10 for holding a calorimeter bomb 12 therein. The vessel is filled with water from tank 14 through conduit means 18, supply valve 20, conduit 22, and first and second vessel filling valves 24 and 26 respectively. As will be described hereinafter, valve 24 supplies a relatively fast flow rate for initially filling the vessel 10 to a first level as determined by a level detecting thermistor 23 mounted to the vessel while valve 26 provides a slow flow rate to top off the filling of the vessel to a second level detected by a second thermistor 25. Both valves 24 and 26 are supplied with pressurized water from pump 16 through conduit 22. Conduit 18 is also coupled to a brass heat sink 28 in thermal contact with a pump motor 30 with a return conduit 29 to tank 14 for circulating water to cool pump 30 minimizing the heat transfer to the system by pump motor 30 which is used for circulating water within the calorimeter vessel as described below. The water circulating loop includes conduit section 32 coupled to pump 30 and to vertically extending conduit 34 coupled to a first inlet hose 36 coupled to the top of vessel 10 for circulating fluid during an analysis. A drain valve 38 is provided for gravity draining water from the vessel after an analysis with air being admitted through a standpipe 22' having a check valve 23' therein. A drain level detector 35 indicates when the vessel has been emptied. Typically, tank 14, pump 16, and valves 20 and 38 will be located below the vessel 10.

Further, conduits 18, 22 and 29 can be coupled to additional identical calorimeter vessels at the locations shown by the broken lines in FIG. 1, although additional separate drain and supply valves (not shown) are employed so that the vessels can be individually filled and emptied. In the preferred embodiment three such vessels are commonly coupled to the supply tank 14 which holds 10 gallons of water for the calorimeter vessels, each vessel of which employs approximately 1,750 cc of water when filled. Also associated with tank 14 is a cooling loop including conduits 11 and 13 between which a heat exchanger 15 with an associated cooling fan 17 is provided to continuously cool the water in the tank to remove energy added due to the operation of the calorimeter vessels. As will become apparent, the actual temperature of the water contained within tank 14 need not be precisely controlled other than to generally maintain it at about room or ambient temperature.

Figure 2:
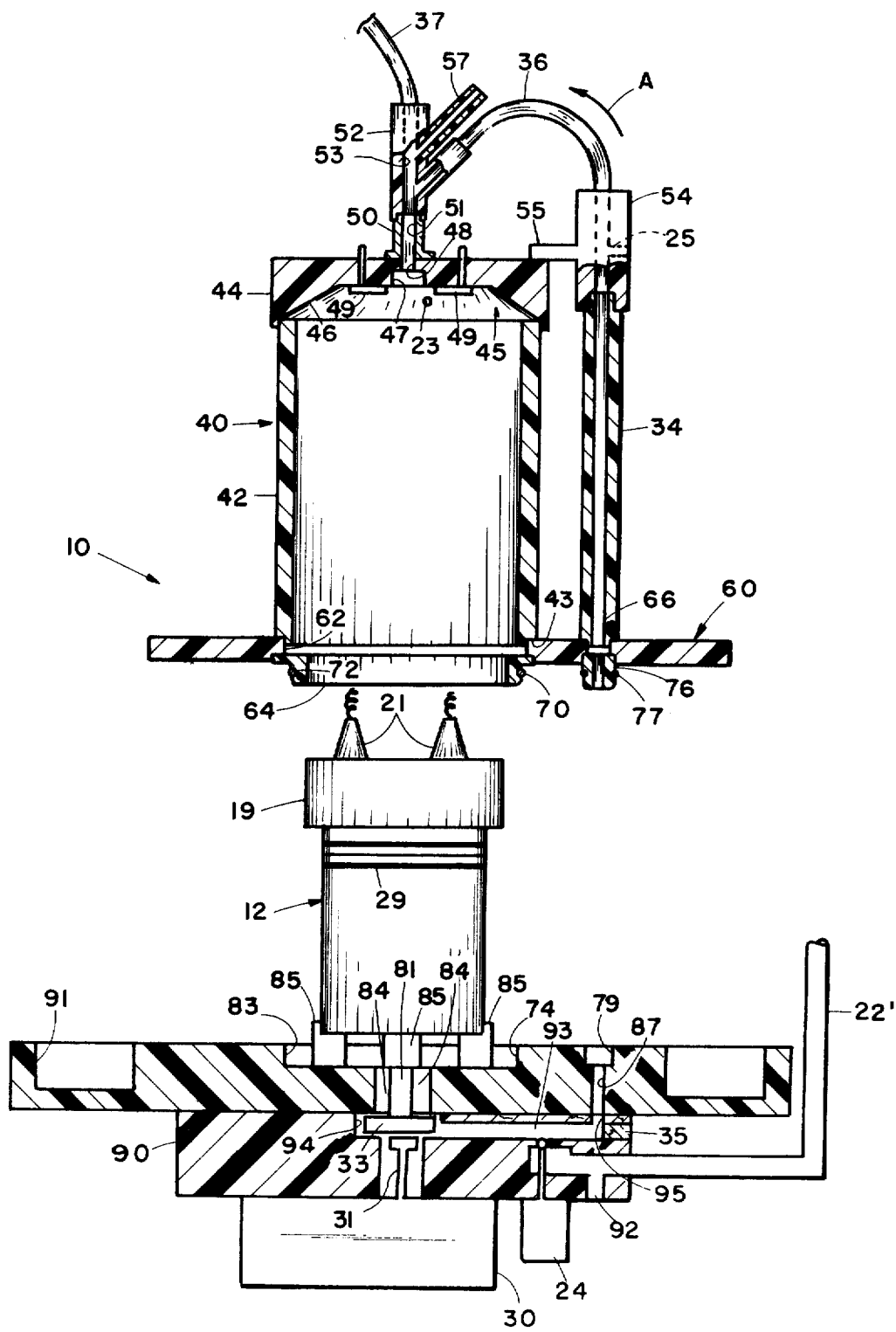
FIG. 2 is an enlarged vertical cross sectional view of a calorimeter vessel embodying the present invention.

FIG. 2 shows one of the identical calorimeter vessels 10 in an open position. The vessel comprises a concavely downwardly opening container 40 which sealably engages a generally rectangular base 80 for supporting the bomb 12 thereon. Container 40 includes a sidewall 42 which in the preferred embodiment is cylindrical and made of a polymeric material such as acrylic or PVC. The upper end of container 40 is sealably enclosed by means of a cap 14 which includes an inwardly tapered and configurated recess 45 having a first conical wall section 46 communicating with cylindrical wall section 47 and a narrowed final cylindrical wall section 48 extending through the top. The first water level sensing thermocouple 23 is mounted to top 44 and is exposed to the conical sidewall 46 for indicating when fluid filling the container 42 has reached this first level approximately midway up wall 46. Top 44 is made of PVC and is permanently sealed to sidewall 42 by means of a conventional bonding adhesive. Mounted in spaced relationship to each other and sealably extending through top 44 are a pair of Ni plated arcuate shaped (170°) electrical contacts 49 which are engaged by contacts 21 and bomb 12 to supply electrical energy through top 44 for igniting the bomb ignition wire. The arcuate shape of the two electrical contacts virtually assures proper contact with the oppositely spaced bomb contacts 21.

Coupled to the cylindrical opening 48 through top 44 is a coupling 50 to which a tube receiving adaptor 52 is mounted. Both adaptor 52 and coupling 50 are made of PVC and are secured to one another by conventional bonding adhesives and include a central opening 51 and 53 respectively, communicating with opening 48 through top 44. A conduit 36 is coupled to one leg of fitting 52 to provide circulating water into the vessel in a direction indicated by arrow A in FIG. 2. A second conduit 37 is coupled to the top of fitting 52 and supplies the trickle flow of water through valve 26 (FIG. 1) to fill vessel 10 to a second level as detected by thermistor 25 mounted to coupling 54 to which tube 36 is also mounted. A breather vent 57 communicates with passageway 53 and permits the passage of air therethrough. Coupling 54 includes a mounting tab 55 bonded to top 44 and is coupled to the vertically extending PVC tube 34 by means of conventional bonding adhesives.

The lower end of cylindrical sidewall 42 of vessel 40 and tube 34 is secured to a movable plate 60 made of PVC and bonded to the sidewall 42 and tube 34 by conventional adhesives. The bottom rim of sidewall 42 includes an annular recess 43 for interfitting into a cylindrical aperture 62 in plate 60 as shown in FIG. 2. An annular PVC ring 64 is bonded to the bottom of plate 60 and includes an annular recess 72 to receive an O-ring or quad seal 70. Seal 70 thus extends below plate 60 and engages the cylindrical sidewall of a recess in base 80 to sealably couple container 40 to base 80 as seen in FIG. 3.

A second annular PVC ring 76 is bonded to plate 60 in alignment with and under aperture 66 formed through plate 60 and communicating with tube 34 to provide a flow path therethrough. An O-ring seal 77 fits within a recess in ring 76 and sealably extends into a cylindrical recess 79 formed in base 80 when the container is closed as seen in FIG. 3. Plate 60 also supports a pair of pneumatically operated cylinders 96 (FIG. 3) for raising and lowering the container 40 with respect to base 80.

Figure 3:
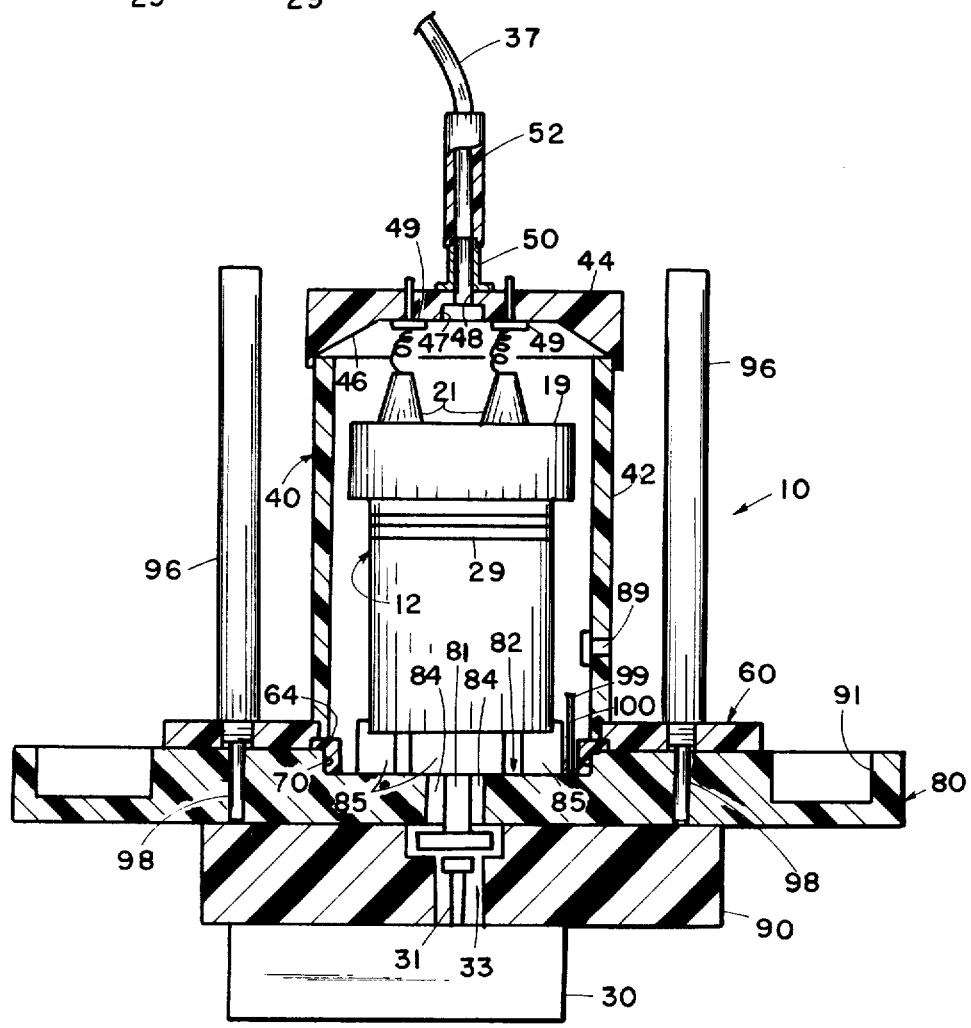
FIG. 3 is a vertical cross sectional view taken along an axis orthoginal to the axis of FIG. 2 showing a calorimeter vessel of the present invention.

Base 80 is also made of PVC and includes a central downwardly extending recess 82 with a cylindrical sidewall 83 permitting seal 70 to sealably couple container 40 to base 80 as shown in FIG. 3. In the center of the floor 86 of recess 82 there is provided four equally spaced cylindrical openings 84 in a ring about center portion 81 extending through base 80 for providing a water flow path to the interior volume of the vessel. Four generally arcuate shaped and equally spaced notched pedestals 85 are positioned in a circle within recess 82 for supporting bomb 12 thereon in vertically spaced relationship above floor 86 of recess 82 as shown. A moat 91 formed downwardly from the top of base 80 surrounds recess 82 for catching residual water which may remain in the event drainage of the vessel is not completed due to a malfunction and the container 40 is opened.

Below base 80 there is provided a PVC pump plate 90 sealably coupled to the base and which includes a water inlet 92 to which conduit 32 (FIG. 1) is coupled and which communicates with an impeller chamber 94 by means of a conduit 93 formed through the plate 90. Conduit 93 also includes a stub section 95 extending upwardly and in communication with a vertically extending aperture 87 in base 80 which, in turn, communicates with tube 34 through seal 78. A motor 30 is mounted to plate 90 and has a drive shaft 31 with a magnet at its end to magnetically couple the shaft to a magnetic impeller 33 rotatably suspended from segment 81 and housed within chamber 94. This drive arrangement thermally isolates the shaft of the electrically operated motor 30 from the calorimeter.

During the initial filling of the vessel, the primary flow path for water is through conduit 32 (FIG. 1), inlet 92, conduit 93 into impeller chamber 94 through valve 24 and upwardly through openings 84 in base 80 into the interior space of the vessel. During this filling period motor 30 is not operating. During operation of motor 30, the associated impeller draws water downwardly through opening 84 and outwardly through conduit 93 and upwardly through conduits 95 and 87 and tube 34, through conduit 36 and through the top of container 40 for circulating water during operation of the calorimeter.

Bomb 12 supported on the pedestal legs 85 is a conventional cylindrical stainless steel vessel having a screw lid 19, the top of which includes spring contacts 21 which are electrically coupled to a conventional internal ignition wire for ignition of a combustible atmosphere and specimen contained therein. Also, the bomb 12 conventionally includes a gas fitting (not shown) for the pressurization of the vessel to approximately 400 PSI of oxygen. Contacts 21 engage contacts 49 as seen in FIG. 3 for providing electrical operating energy for the ignition wire. The bomb is of conventional construction and of the type generally used in calorimeters with the exception of bar code stripes 29 around the side thereof to uniquely identify each bomb employed with the calorimeter of the present invention. Indicia 29 is scanned by a photo-optical detector 89 (FIG. 3) sealably mounted through the sidewall 42 of the vessel as it is lowered to provide a signal uniquely identifying a particular bomb. This signal is then used to correlate the bombs calibration number (corresponding generally to its thermal mass) automatically such that the electrical circuit associated with the calorimeter vessel can provide a correction factor for each of the several bombs which can be employed in the calorimeter.

Referring now to FIG. 3, the means by which the container is opened and closed is disclosed and comprises a pair of cylinders 96 threadably secured to plate 60 and having pistons 98 which have their ends secured to base 80. Actuation of the double acting cylinders 96 in one direction therefore causes plate 60 to move away from base 80 to open the vessel to the position shown in FIG. 2. The piston 96 and rods 98 serve as guide and support means for the container when opened. To close the vessel the double acting cylinders 96 are activated in an opposite direction to draw the pistons 98 therein and lower the container into the position shown in FIG. 3 whereupon the system is again sealed for use.

A conventional temperature detecting nickle wire 99 is mounted to an insulated pedestal 100 (FIG. 3) extending upwardly from the floor 86 of recess 82 such that the temperature of water within the vessel can be measured to determine the energy content of the sample contained within bomb 12. The structural elements of the calorimeter are made of a polymeric material such as PVC to minimize heat transfer in the calorimeter with respect to the surroundings. Further, the vessel 10 shown in FIGS. 2 and 3 is mounted in a cabinet insulated with suitable closed cell foam material to further isolate the calorimeter from ambient temperature variations which may occur. Having described the physical structure of the improved vessel itself, a description follows of the electrical control circuit employed for controlling the operation of the calorimeter.

Figure 4:
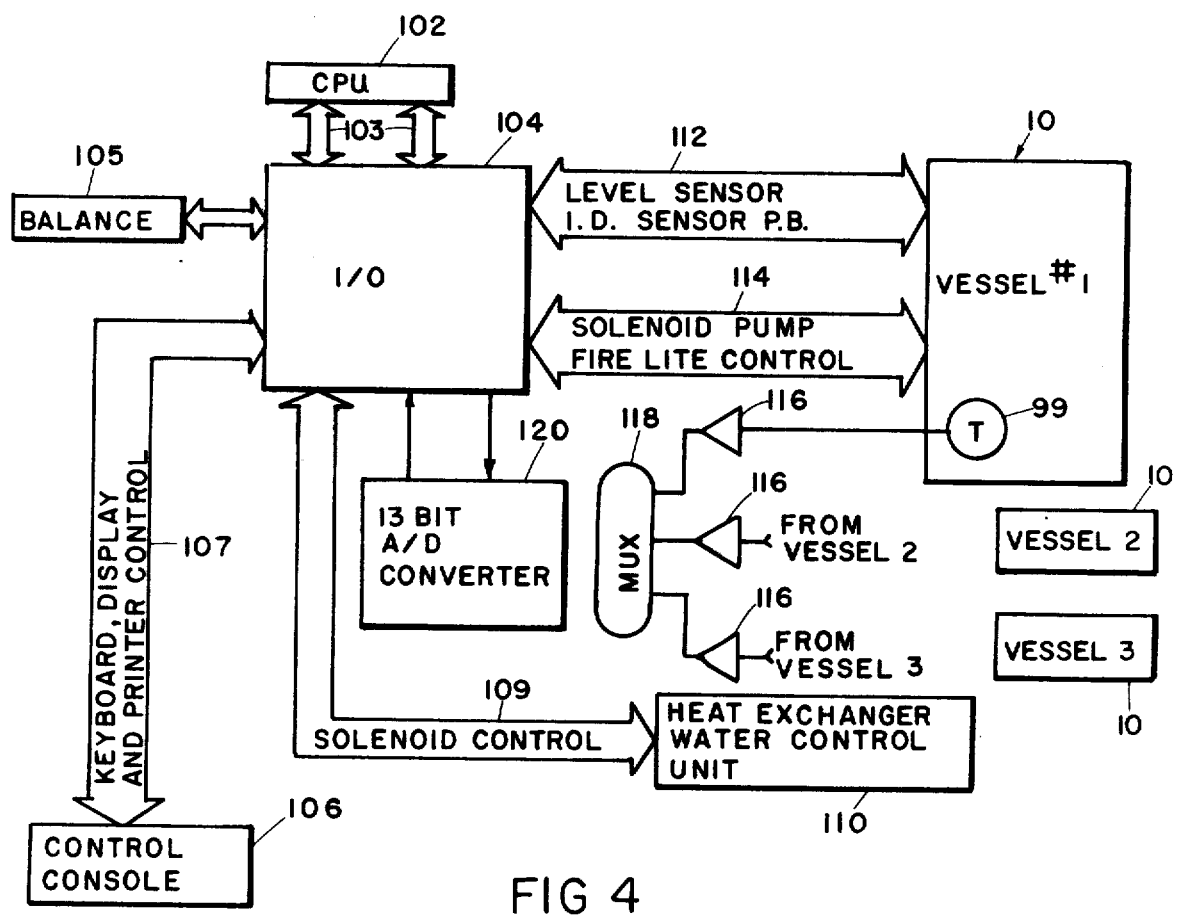
FIG. 4 is a circuit diagram in block form of the electrical control circuit of the present invention.

FIG. 4 shows the electrical control circuit which includes a microprocessor 102 including a CPU and ROM and RAM memory circuits. In the preferred embodiment, an Intel 8085 commercially available microprocessor was employed and coupled by data links 103 to an input/output circuit 104. Circuit 104 interfaces the microprocessor with the various detectors and control elements of the calorimeters. A digital balance 105 for weighing a sample and providing digital weight representative signals to the microprocessor is coupled to one input of circuit 104. A control console 106 including a keyboard and a printer is also coupled to the microprocessor through circuit 104 by means of a data link 107 intercoupling the console 106 with circuit 104. The microprocessor is coupled to the heat exchanger 15, 17 (FIG. 1), pump 16 and the valves shown in FIG. 1 (a circuit shown schematically in FIG. 4 as unit 110) by means of data link 109 and circuit 104. The sensors such as sensors 23, 25, 35 and 89 associated with each of the vessels are coupled to circuit 104 through data links 112 while the bomb igniter wire, pump motor 30, and its associated indicator lights on each of the vessels 10 are coupled to circuit 104 via data links 114. Fianlly, the temperature sensor 99 associated with each of the three vessels of the system of the preferred embodiment are coupled to the input/output circuit 104 through first a chopper stabilized amplifier 116, a multiplexer 118 and a 13 bit A/D converter 120 which converts the analog signals from the temperature measuring circuit 99 into a digital format for the microprocessor 102. It is noted that temperature detecting means 99 includes the nickle wire electrically mounted in a conventional temperature compensating bridge circuit such that the signals from circuit 99 shown in FIG. 4 which are applied to amplifiers 116 are an analog voltage representative of the actual temperature of the water surrounding the nickle wire mounted on pedestal 100 (FIG. 3).

By use of a microprocessor with data storage means it is possible to calibrate each of several bombs 12, each identified with a unique code 29, and store the calibration factor for each bomb used in the system. Also, by providing temperatures read from temperature detecting means 99, it is not necessary as in a conventional isothermal calorimeter to wait until the initial temperature curve is stabilized. Thus, it is possible to fire the bomb approximately only 3 minutes after the filling of the container as opposed to 15 to 20 minutes as required in conventional calorimeters. By periodically sampling the water temperature in the vessel, and the change in the slope of the increasing temperature readings at predetermined times ($t_2$ and $t_3$ FIG. 7) an initial temperature $T_4$ can be computed which is slightly higher than the temperature would be if simply extrapolated. This is done to compensate for the additional energy initially remaining in the system since the bomb is fired before the temperature stabilizes. This computation generally follows the following equation:

$$T_4 = T_3 + \Delta t \times \text{slope } t_3 \times CF$$

where $T_3$ is the temperature at firing, $\Delta t$ is 1 second, slope $t_3$ is the change in temperature occuring at time $t_3$ (i.e., the slope of the temp curve at $t_3$) and CF is the empirically determined correction factor. Typical units where 4000 counts from circuit 120 represent 1° C. are:

$T_3 = 41,420$ counts slope $t_3 = 139$ counts/min.

C.F. $= 67$ counts

Further, the end temperature ($T_e$) after firing of the bomb can also be determined by conventional algorithms again by sampling temperature data until such time as the change in temperature becomes constant near the end of the cycle of operation. The programming of the microprocessor and the operation of the calorimeter is shown in the flow diagrams of FIGS. 5, 6, and the chart of FIG. 7 now described.

Figure 5:
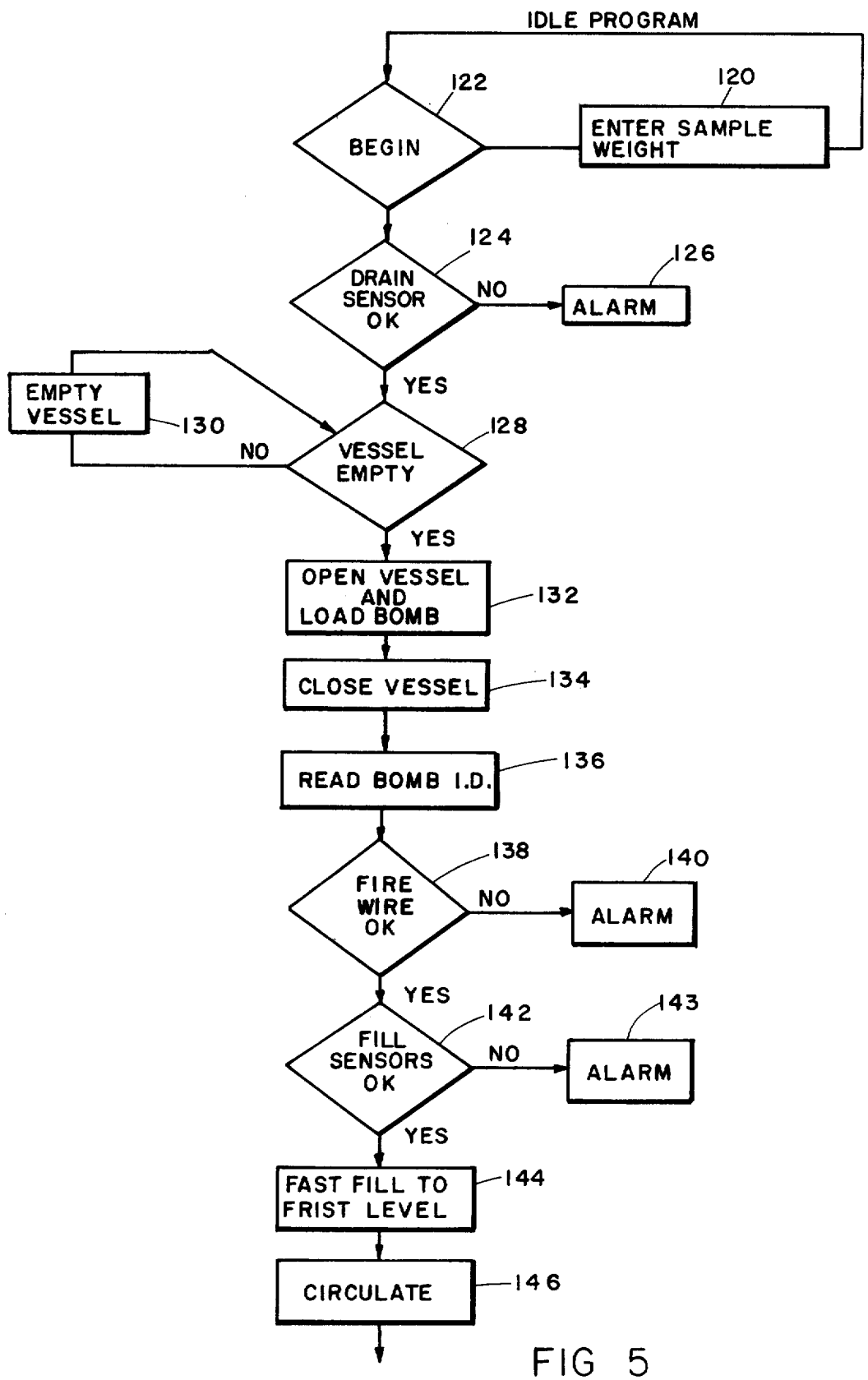
FIGS. 5 and 6 are flow diagrams of the operation of the system of the present invention.

The calorimeter operation is initiated by weighing the sample using digital balance 105 and entering the sample weight into the computer memory as indicated by block 120 (FIG. 5). The sample can then be physically placed in the bomb together with the igniting fuse and the bomb is sealed and pressurized with oxygen to approximately 400 PSI. A push button start switch on the control console 106 is then actuated beginning the cycle of operation indicated by block 122 in FIG. 5. The vessel empty sensor 35 (FIG. 1) is then tested as indicated by block 124 to ascertain its operational state. In the event the sensor is open or short circuited, an alarm is activated indicating to the operator that the drain sensor is not operational and should be replaced. If the sensor is operational, its output signal is tested to ascertain whether or not the vessel has been drained of water as indicated by block 128. This test is conducted to ascertain whether or not the vessel can be opened for inserting the bomb.

In the event the vessel is not empty, a signal from circuit 102 actuates valve 38 to open to permit draining of the vessel into tank 14 (FIG. 1) as indicated by block 130. Valve 38 and the remaining valves, pumps and cylinders are solenoid operated and controlled by signals from the microprocessor through input/output circuit 104 and data link 114. Once sensor 35 indicates the vessel is empty, it is opened by actuation of cylinders 96 (FIG. 3) and the bomb loaded onto the pedestals 85 as indicated by block 132 in FIG. 5. Next, the operator actuates a close switch on the control console 106 (FIG. 4) and as indicated by block 134, cylinders 96 are actuated to close the vessel to the position shown in FIG. 3. As the vessel closes the photo-optical scanner 89 scans the indicia 29 on the side of the bomb to identify the particular bomb being used in the calorimeter. The data identifying the bomb is thus read by the computer and entered into memory as indicated by block 136.

The continuity of the firing wire associated with the bomb is then tested as indicated by block 138, and if it is open or the circuitry connecting the fuse wire to the firing circuit is open, an alarm is sounded as indicated by block 140. If it is operational, the fill sensors 23 and 25 are next tested as indicated by block 142 to ascertain their operational state. If either the sensors are inoperative an alarm is sounded as indicated by block 143. These tests are conducted by the computer checking the contunity of the sensors and the fuse wire through data links 112 and 114 and circuit 104. With the vessel closed and the sensors and fuse operational, valves 20 and 24 and pump 16 are activated by signals from data link 114 to fill the vessel until such time as water engages sensor 23 as indicated by block 144. This is a relatively fast fill requiring only approximately 15 seconds to complete. Pump 16 provides fluid pressure not only to valve 24 through conduit 22 and valve 20, but also to supply cooling water through heat exchanger 28 associated with pump 30. After the first fill level has been achieved, valves 20 and 24 are closed and pump 30 is activated for a period of approximately 10 seconds to permit air bubbles to escape the system through bleeder vent 57 (FIG. 2) at the top of the vessel above the level of sensor 25 mounted to coupling 54. This circulation step is indicated by block 146 of FIG. 5.

Figure 7:
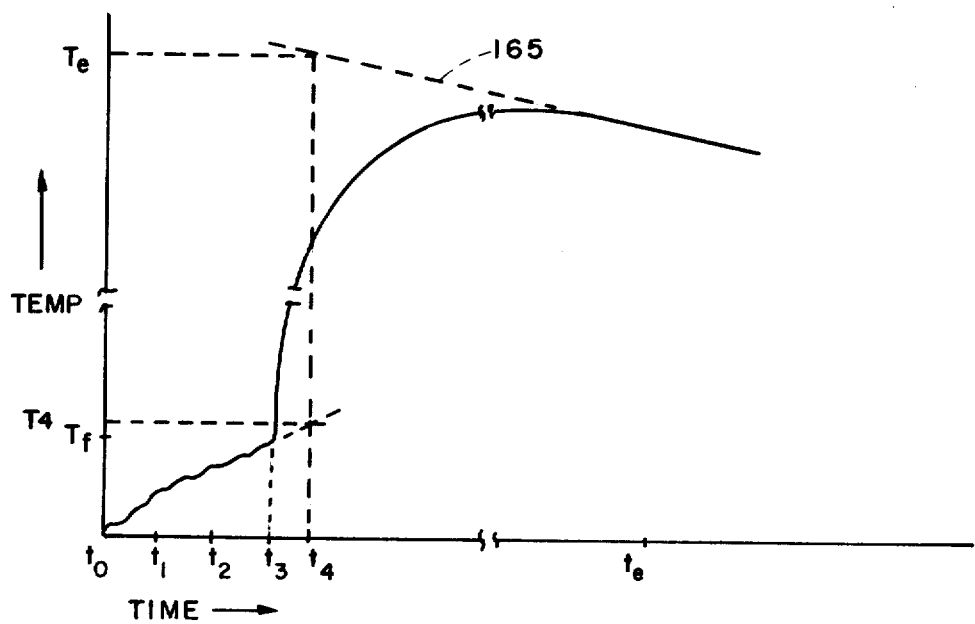
FIG. 7 is a graph showing the time versus temperature detected during operation of the calorimeter of the present invention.
Figure 6:
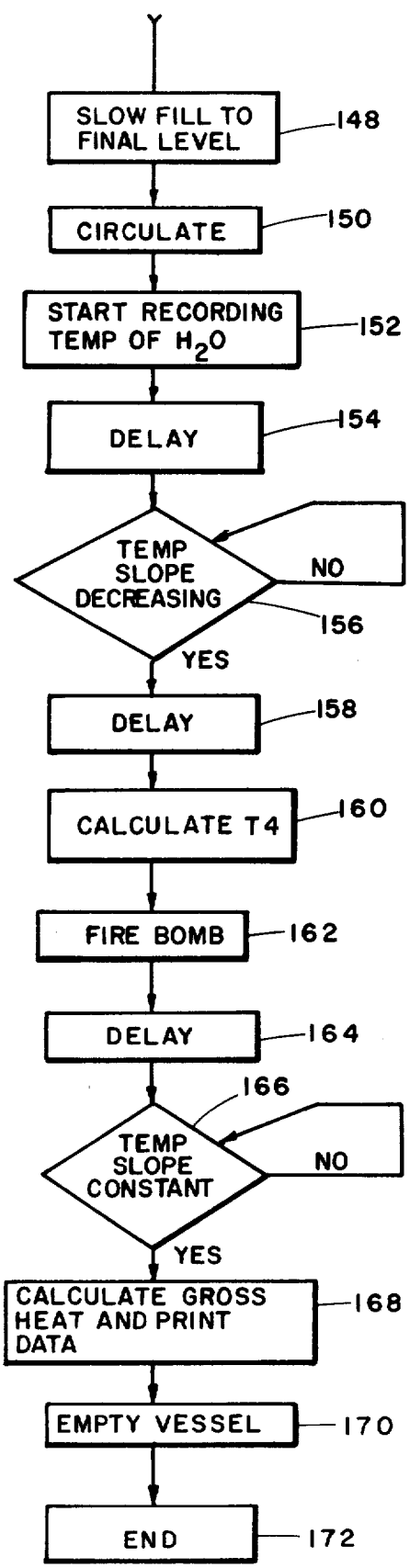

Next, the operational sequence proceeds as shown in FIG. 6 by the deactivation of pump 30 and the activation of valves 20 and 26 to fill the vessel to its final level whereupon water reaches the level of sensor 25 mounted on coupling 54. This step is indicated by block 148 of FIG. 6 and takes only about 20 seconds since the filling volume is small. After filling to the final level in which approximately 1,750 cc of fluid is in the calorimeter vessel, valves 20 and 26 are closed and pump 30 is again actuated for a period of approximately 20 seconds to equalize the water temperature and remove air bubbles as indicated by block 150 (FIG. 6). The end of this time period corresponds to time $t_0$ shown in FIG. 7 and the signals from the temperature detecting unit 99 are stored in memory at 6 second periodic intervals. The periodic temperature recording as indicated by block 152 and continues throughout the remainder of each operating cycle of the calorimeter. A 2 minute delay timer is then run as indicated by block 154 after which the temperature (shown in solid lines in the time-temperature graph of FIG. 7) difference between adjacent temperature samples is tested to ascertain whether or not the change of the slope of the increasing temperature (due to water movement and thermistor heat of the sensors within the system and the differential between the water and ambient temperatures) curve has stopped increasing and started decreasing (i.e., the second differential of the time-temperature curve is 0 or negative). This test is conducted on the temperature data applied to the microprocessor with a standard algorithm subroutine in the microprocessor as indicated by block 156. Once the temperature slope begins decreasing, a 1 minute delay timer indicated by block 158 runs to reach the firing time at time $t_3$. During the time $t_2$ and the initial $t_3$, temperature $T_4$ is calculated based upon the stored temperature data as noted earlier and assigned to time $t_4$ as indicated by dashed lines in FIG. 7. $T_4$ is one of the two temperatures employed in the calculation of the heat of combustion of the specimen as described below. This calculation step is indicated by block 160 in FIG. 6. The use of the microprocessor in analyzing the slope of changing temperature data permits firing of the bomb well prior to the actual temperature slope becoming constant. Thus, for example, the bomb is typically fired at $t_3$ approximately 3 minutes after the last filling and circulating step has been completed ($t_o$) instead of, for example, 15 to 20 minutes later. After the one minute delay indicated by block 158, the microprocessor provides a firing signal to the bomb ignition wire through circuit 104 and data link 114 which causes ignition and complete combustion of the specimen. Heat from this reaction naturally begins heating the water as indicated by the time-temperature graph of FIG. 7 and a 6 minute timer is set as indicated by block 164 after which a test is conducted to ascertain whether or not the temperature slope has become constant as indicated by block 166. During this period of time, pump 30 is actuated to continuously circulate water past the bomb and sensor 99 assuring uniform water temperature. By sampling the periodic temperature data to ascertain when, after the peak temperature has been reached and the declining temperature slope toward the end of the time temperature curve has reached a steadily declining level, the constant slope is detected. It is noted that the time and temperature axis of the graph shown in FIG. 7 are broken to indicate, for example, that the initial temperature changes are in a matter of hundredths of a degree while the end temperature $T_e$ can be 2° to 3° higher. Further, the ending time $t_e$ can be several minutes after time $t_3$ of firing although 6 minutes is typical.

If the temperature slope is constant, $T_e$ is calculated by extrapolating rearward to as $t_4$ indicated by dashed line 165 in FIG. 7 by the microprocessor using a algorithum to determine the temperature $T_e$ which is used for determining the heat of combustion of the specimen.

The heat of the specimen is determined by the standard equation comprising:

$$Q=(T_e-T_4)\times(W\times F_1\times F_2)-e_1-e_2-e_3$$

where: Q is the heat of combustion or energy content of the sample either in BTU's per pound in the preferred embodiment or scaled for calories per gram of megajoules per kilogram if desired; W is the weight of the specimen in grams, $F_1$ is an empirically determined calibration factor corresponding to the thermal mass of the vessel and comprises a number which can be determined by running a known specimen in the system and storing the number in the storage circuit means associated with the microprocessor; $F_2$ is an empirically determined calibration factor corresponding to the thermal mass of the bomb with such calibration information stored for each bomb uniquely identified by the identifying indicia 29 on the bomb; and $e_1$, $e_2$, and $e_3$ are the standard correction factors for the heat of formation of HNO₃, H₂SO₄, and the heat of combustion of the fuse respectively, all of which are stored in the microprocessor memory. The algorithm for providing this simple mathematical calculation is conventionally programmed into the microprocessor and the resultant data is then supplied through the input/output circuit 104 and data line 107 to the control console 106 and printed for the operator to provide a permanent record of the heat of combustion of the sample. Naturally, if desired, a sample identification number can be keyed into the system such that each printout will include a sample identification number associated with the sample being run. Subsequent to the calculation and data printout step indicated by block 168 in FIG. 6, the vessel is emptied by the activation of the drain valve 38 and deactivation of pump 16. After emptying as indicated by block 170, the analysis of the sample has been completed as indicated by block 172 and the vessel can be opened and a new analysis run starting with block 122 of FIG. 5.

Thus, the calorimeter of the present invention provides a closed system in which water need not be manually handled and which provides precise, accurate and automatic filling of the calorimeter vessel. Further, the calorimeter of the present invention provides for relatively fast analysis of a sample by not only rapidly filling the vessel with water but also by permitting firing of the calorimeter bomb relatively quickly after the vessel has been filled. Since several vessels can be employed, during an analysis in one vessel, another vessel can be emptied while a third loaded with a bomb. Thus, the sample throughput of the system is high permitting, for example, 15 samples to be run in one hour.

It will become apparent to those skilled in the art that various modifications to the system of the preferred embodiment described herein can be made without departing from the spirit or scope of the invention as defined by the appended claims.

The embodiments of the invention in which an exclusive property or privilege is claimed are defined as follows:

1. A calorimeter vessel for receiving a sample holding calorimeter bomb comprising:
   base means defining a support for a calorimeter bomb including means for supplying water therethrough at a first flow rate;
   a container having sidewalls and being substantially enclosed at one end and open at an opposite end, said open end of said container sealably engagable with said base means with said sidewalls circumscribing said water supply means;
   means for moving said container with respect to said base means for opening and closing said vessel defined thereby; and
   conduit means coupled to said container at an end remote from said open end to provide a second lower flow rate of water to said vessel.

2. The vessel as defined in claim 1 wherein said container is generally vertically oriented and defines a concavely opening chamber extending downwardly.

3. The vessel as defined in claim 2 and further including water level detection means associated with said container at first and second levels, and control means coupled to said water supply means, to said conduit means, and to said detection means for supplying water initially to said first level at a first rate and subsequently to said second level at said second flow rate.

4. The vessel as defined in claim 1 wherein said container includes means for identifying a calorimeter bomb placed therein.

5. The vessel as defined in claim 4 wherein each bomb employed in connection with said vessel includes a code indicia and wherein said identifying means comprises a reader mounted to said container for reading the information contained by said indicia.

6. A calorimeter vessel for receiving a sample holding calorimeter bomb comprising:
   base means defining a support for a calorimeter bomb including means for supplying water therethrough;
   a container having sidewalls and being substantially enclosed at one end and open at an opposite end, said open end of said container sealably engagable with said base means with said sidewalls circumscribing said water supply means wherein said container is generally vertically oriented and defines a concavely opening chamber extending downwardly;
   means for moving said container with respect to said base means for opening and closing said vessel defined thereby; and
   water level detection means associated with said container at first and second levels, and control means coupled to said water supply means and to said detection means for supplying water initially to said first level at a first rate and subsequently to said second level at a second flow rate, wherein said water supply means includes aperture means extending through said base for providing a first flow path of water and conduit means coupled to said container at an end remote from said open end to provide a second lower flow rate of water to said vessel.

7. The vessel as defined in claim 6 and further including means for circulating water through said vessel comprising pump means coupled to remove water from one end of said vessel, and conduit means extending from said pump to an opposite end of said vessel for circulating water through said vessel during an analysis.

8. The vessel as defined in claim 7 wherein said means for moving said container with respect to said base comprises a pair of cylinder means extending between said base and said container for raising and lowering said container with respect to said base.

9. The vessel as defined in claim 8 and further including a moat formed downwardly in said base and circumscribing the periphery of said container.

10. The vessel as defined in claim 9 and further including drain means coupled to said base for draining water therefrom.

11. A calorimeter vessel for receiving a sample holding calorimeter bomb comprising:
   base means defining a support for a calorimeter bomb;
   a downwardly opening concave container sealably engagable with said base means;
   cylinder means extending between said base and said container for moving said container with respect to said base means for selectively opening and closing said vessel defined thereby and sealing said vessel when in a closed position; and
   means for supplying water to said vessel to fill said vessel to a first level at a first flow rate and subsequently to a second level at a second rate slower than said first rate.

12. The vessel as defined in claim 11 and further including water level detection means associated with said container at first and second levels, and control means coupled to said water supplying means and to said detection means for supplying water initially to said first level at said first rate and subsequently to said second level at said second flow rate.

13. The vessel as defined in claim 12 wherein each bomb employed in connection with said vessel includes a code indicia and wherein said identifying means comprises a reader mounted to said container for reading the information on said indicia.

14. The vessel as defined in claim 11 wherein said container includes means for identifying a calorimeter bomb placed therein.

15. A calorimeter vessel for receiving a sample holding calorimeter bomb comprising:
base means defining a support for a calorimeter bomb;
a downwardly opening concave container sealably engagable with said base means;
means for moving said container with respect to said base means for opening and closing said vessel defined thereby;
means for supplying water to said vessel to fill said vessel to a first level at a first flow rate and subsequently to a second level at a second rate slower than said first rate;
water level detection means associated with said container at first and second levels, and control means coupled to said water supplying means and to said detection means for supplying water initially to said first level at said first rate and subsequently to said second level at said second flow rate, wherein said water supply means includes aperture means extending through said base for providing a first flow path of water; and
conduit means coupled to said container at an end remote from said open end to provide a second lower flow rate of water to said vessel.

16. The vessel as defined in claim 15 wherein said means for moving said container with respect to said base means comprises a pair of cylinder means extending between said base and said container for raising and lowering said container with respect to said base.

17. The vessel as defined in claim 16 and further including means for circulating water through said vessel comprising pump means coupled to remove water from one end of said vessel, and conduit means extending from said pump to an opposite end of said vessel for circulating water through said vessel during an analysis.

18. A calorimeter control system comprising:
temperature detecting means positioned within a calorimeter vessel, circuit means coupled to said temperature detecting means for sampling the temperature within the calorimeter vessel at periodic intervals and for storing data representing the detected temperature readings, said circuit means including a microprocessor programmed to correlate said temperature data with system parameters to predict the initial temperature prior to reaching a constant temperature slope to permit early firing of the calorimeter bomb and correlating said data including the end temperature for the determination of the heat content of a sample.

19. The system as defined in claim 18 wherein said circuit means includes a microprocessor.

20. The system as defined in claim 19 wherein said calorimeter vessel includes means for supplying water thereto at different rates and wherein said system further includes water level detecting means coupled to said microprocessor for controlling said water supplying means.

21. A calorimeter system comprising a plurality of calorimeter vessels each including base means for supporting a calorimeter bomb thereon and a container sealably mounted to the base and movable between open and closed positions for loading the bomb within the vessel so formed and for conducting an analysis respectively;
a common supply of water and conduit means coupling said supply to each of said vessels, said conduit means including control valve means;
control means for actuating said control valve means for selectively filling and emptying each of said vessels with water;
water level detection means associated with each of said containers at first and second levels, wherein said control means is coupled to said detection means for actuating said control valves for supplying water initially to said first level at a first rate and subsequently to said second level at a second flow rate; and
means for circulating water through each of said vessels comprising pump means coupled to remove water from one end of said vessel, and conduit means extending from said pump to an opposite end of said vessel for circulating water through each of said vessels during an analysis.

22. The system as defined in claim 21 and further including means for moving said container with respect to said base comprising a pair of cylinder means extending between said base and said container for raising and lowering said container with respect to said base.

23. The system as defined in claim 22 wherein each of said containers includes means for identifying a calorimeter bomb placed therein.

24. The system as defined in claim 23 wherein each bomb employed in connection with said vessel includes a code indicia and wherein said identifying means comprises a reader mounted to said container for reading the information contained by said indicia.

25. The system as defined in claim 24 and further including a moat formed downwardly in said base and circumscribing the periphery of said container.

* * * * *